(12) United States Patent
Noack et al.

(10) Patent No.: US 7,276,632 B2
(45) Date of Patent: Oct. 2, 2007

(54) METHOD FOR THE PRODUCTION OF 2,3-CIS-SUBSTITUTED 2-ARYL PROPENALS

(75) Inventors: Rainer Noack, Großthiemig (DE); Lothar Rüb, Speyer (DE); Clemens Palm, Dresden (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/581,033

(22) PCT Filed: Dec. 14, 2004

(86) PCT No.: PCT/EP2004/014241

§ 371 (c)(1),
(2), (4) Date: May 30, 2006

(87) PCT Pub. No.: WO2005/056498

PCT Pub. Date: Jun. 23, 2005

(65) Prior Publication Data

US 2007/0093681 A1      Apr. 26, 2007

(30) Foreign Application Priority Data

Dec. 15, 2003   (DE)   ................ 103 58 655

(51) Int. Cl.
*C07C 45/72*   (2006.01)
(52) U.S. Cl. .................................... 568/433
(58) Field of Classification Search ................ 568/433
See application file for complete search history.

(56) References Cited

U.S. PATENT DOCUMENTS

| 4,920,232 A | 4/1990 | Goetz et al. |
| 5,098,917 A | 3/1992 | Seele et al. |

FOREIGN PATENT DOCUMENTS

| DE | 37 22 886 A1 | 1/1989 |
| DE | 38 25 586 A1 | 2/1990 |
| EP | 0 352 675 A2 | 1/1990 |

OTHER PUBLICATIONS

Houben-Weyl, Höhere Aldehyde durch Aldokondensationen, Methoden der organischen Chemiei, Band VII/1, 1954, pp. 76-96, Georg-Thieme-Verlag, Stuttgart, Germany.
Kurt Alder et al., Darstellung einiger 1,2-disubstituierter Deine und ihre Verwendung zu Dien-Synthesen, Annalen der Chemie, 1954, Band 56, pp. 110-136.
Wilhelm Treibs et al., Über einige Adol- und Kondensationsreaktionen de Phenylacetaldehyds, Chemische Berichte, 1952, vol. 85, pp. 1116-1119.
J.L.E. Erickson et al., The Spontaneous Polymerization of Phenylacetaldehyde, Journal of the American Chemical Society, 1958, vol. 80, pp. 5466-5469.
Beilstein Institut Für Förderung Der Chemischen Wissenschaften, Beilstein Reaction nr: 2044673, Jun. 27, 1998, Frankfurt am Main, Germany.
Paul Schorigin et al., Aldehyde vom Typus des Zimtaldehyds, II.Mitteil.: α-Phenyl- und α- Benzyl-zimtaldehyd, 1933, vol. 66, pp. 389-393.
Pierre Courtot et al., Photocycloaddition selon un mod [4πs = 2πa]chez le E,Z,E diphyényl-2,6 ç-tolyl-1 hexatriène-1,3,5, J. Chem. Res. Miniprint, 1981, vol. 10, pp. 3516-3528.
M.J. Climent et al., Aldol Condensations on Solid Catalysts: A Cooperative Effect between Weak Acid and Base Sites, Advance Synthetic Catalysts, 2002, vol. 344-10, pp. 1090-1096.
Ji-Hyun Kim et al., A Tandem Epoxide Isomerization-Aldol Condesation Process Catalyzed by Palladium Acetate-Tributylphosphine, Journal of Organic Chemistry, 1996, vol. 61, pp. 7656-7657.
Robert L. Stern et al., Enazine Chemistry II. The Mechanism of Formation of 1-(*cis* -3-Phenylpropenyl)-5-phenypyrazole from the Pyrolysis of Cinnamaldehyde Azine (1).

*Primary Examiner*—Sikarl A. Witherspoon
(74) *Attorney, Agent, or Firm*—Birch, Stewart, Kolasch & Birch, LLP

(57)   ABSTRACT

The invention relates to a method for producing 2,3-cis-substituted 2-aryl propenals by condensing a 2-aryl acetaldehyde I with a non-enolizable aldehyde compound II in the presence of a base. The inventive method is characterized in that the reaction is carried out in a solvent mixture comprising at least one water-miscible organic solvent and water at a volume ratio $V_{solvent}{:}V_{water}$ ranging between 10:1 and 0.5:1.

20 Claims, No Drawings

METHOD FOR THE PRODUCTION OF 2,3-*CIS*-SUBSTITUTED 2-ARYL PROPENALS

The present invention relates to a process for preparing 2,3-cis-substituted 2-arylpropenals by condensing a 2-arylacetaldehyde I with a nonenolizable aldehyde compound II in the presence of a base.

2,3-cis-substituted 2-arylpropenals, especially the diphenylpropenals substituted in the 3-position with a further aryl group, serve to prepare hydroxymethyloxiranes which are in turn required in the synthesis of active fungicidal ingredients.

For the preparation of such substituted propenals, various processes are known, in which the use of specific catalyst systems is generally necessary.

It is known that 2,3-substituted propenals may be prepared by means of a crossed aldol condensation. Such reactions are generally carried out in an organic solvent or, optionally, when suitable reactants are used, without solvent. However, depending on the structure and reactivity of the aldehydes used, not only the desired products having cis-configuration, but frequently also considerable fractions of by-products (see, for example, Houben-Weyl, Methoden der organischen Chemie, volume VII/1, Georg-Thieme-Verlag, Stuttgart, 1954, 76ff; Alder et al., Ann. Chem. 586, 1954, 110).

A further difficulty consists in often low overall yields of the reaction. These are presumed to be a consequence of the high sensitivity of the reaction products toward acids and bases. For instance, DE 38 25 586 describes the preparation of substituted 2,3-bis(phenyl)propenals such as E-2-(4-fluorophenyl)-3-(2-trifluoromethylphenyl)-propenal by means of crossed aldol condensation with a yield of only 65%. The difficulties outlined also apply in a similar manner in DE 37 22 886 which describes the reaction of ring-substituted phenylacetaldehydes with a further aldehyde compound. The question of stereoselectivity is not addressed there. The reaction is effected in an organic solvent.

In the case of the 2-phenylalkanals, the nature of the resulting by-products has been investigated in more detail. A tendency toward self-condensation to form dimeric and/or trimeric oligomers and mixed trimers has been detected. Specifically, Treibs et al., Chem. Ber. 85, 1952, 1116 identified triphenylpyran derivatives and their subsequent products; and Ericksen et al., J. Am. Chem. Soc. 80, 1958, 5466, identified aldoxanes and their subsequent products as specific trimers.

The formation of by-products, as described, leads to a minimization in the yields of the desired 2,3-cis-substituted 2-arylpropenals. In general, the presence of undesired by-products leads to considerable difficulties in the workup of the products of value. There is therefore a need for an economically viable process for preparing 2,3-cis-substituted 2-arylpropenals.

It is an object of the present invention to provide a process for preparing 2,3-cis-substituted 2-arylpropenals which avoids the disadvantages of the prior art. The process should in particular afford the desired 2,3-cis-substituted 2-arylpropenals with high yields and simultaneously high stereoselectivity. In addition, it should substantially avoid the formation of by-products, and also enable technically simple implementation.

We have found that this object is achieved by reacting a 2-arylacetaldehyde I with a nonenolizable aldehyde compound II in the presence of a base in a solvent mixture which comprises at least one water-miscible organic solvent and water in a predefined volume ratio.

The present invention thus relates to a process for preparing 2,3-cis-substituted 2-arylpropenals by condensing a 2-arylacetaldehyde I with a nonenolizable aldehyde compound II in the presence of a base, which comprises carrying out the reaction in a solvent mixture which includes at least one water-miscible organic solvent and water in a $V_{solvent}:V_{water}$ volume ratio of from 10:1 to 0.5:1 and in particular from 5:1 to 0.5:1.

The term "2,3-cis-substituted 2-arylpropenals" refers here and hereinbelow to a cis-configuration of the 2-arylpropenals according to the invention with regard to the aryl group in the 2-position and a further substituent other than hydrogen in the 3-position. The term "cis-configuration" used here and hereinbelow is also to be regarded synonymously. With regard to the position of aldehyde group and substituent in the 3-position, they are the E-isomers.

The aryl group of the 2-arylacetaldehydes I used in accordance with the invention typically includes an optionally substituted aromatic hydrocarbon radical such as phenyl, naphthyl or anthryl, in particular phenyl.

In addition, the aryl group of the 2-arylacetaldehydes I used in accordance with the invention may have one or more, for example 1, 2, 3, 4 or 5, R' substituents which are each independently selected from $C_1$-$C_{10}$-alkyl which optionally has one or more substituents other than alkyl which may be selected from fluorine, chlorine, bromine, iodine, $C_1$-$C_{10}$-alkoxy and $C_3$-$C_{10}$-cycloalkyl;

$C_1$-$C_{10}$-alkoxy which optionally has one or more substituents other than alkyl which may be selected from fluorine, chlorine, bromine, iodine, $C_1$-$C_{10}$-alkoxy and $C_3$-$C_{10}$-cycloalkyl;

$C_3$-$C_{10}$-cycloalkyl which optionally has one or more substituents other than alkyl which may be selected from fluorine, chlorine, bromine, iodine and $C_1$-$C_{10}$-alkoxy;

phenoxy which is optionally substituted by 1,2,3,4 or 5 groups selected from $C_1$-C4-alkyl, $C_1$-$C_4$-alkoxy, fluorine, chlorine, bromine and iodine;

halogen which is selected from fluorine, chlorine, bromine and iodine;

$C_1$-$C_{10}$-acylamino; and a nitro group.

Here and hereinbelow, alkyl is a linear or branched, aliphatic hydrocarbon radical having generally from 1 to 10, in particular from 1 to 6 and especially from 1 to 4, carbon atoms, for example methyl, ethyl, n-propyl, 1-methylethyl, n-butyl, 1-methylpropyl, 2-methylpropyl or 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, n-heptyl, n-octyl, n-nonyl, n-decyl, 1-methylhexyl, 1-ethylhexyl, 2-ethylhexyl, 1-methylheptyl, 1-methyloctyl, 1-methylnonyl. The alkyl radicals mentioned may have one or more, for example 1, 2, 3 or 4, substituents other than alkyl which may be selected from halogen, e.g. fluorine, chlorine, bromine or iodine, $C_1$-$C_{10}$-alkoxy as in $C_1$-$C_{10}$-alkoxy-$C_1$-$C_{10}$-alkyl, e.g. 2-methoxyethyl, or $C_3$-$C_{10}$-cycloalkyl as in $C_3$-$C_{10}$-cycloalkyl-$C_1$-$C_{10}$-alkyl, e.g. cyclohexylmethyl.

Here and hereinbelow, halogen is a halogen atom which is selected from fluorine, chlorine, bromine and iodine.

Here and hereinbelow, alkoxy is an alkyl radical as defined above bonded via an oxygen atom, generally having from 1 to 10, in particular from 1 to 6 and especially from 1 to 4, carbon atoms, for example methoxy, ethoxy, propoxy, 1-methylethoxy, butoxy, 1-methylpropoxy, 2-methylpropoxy or 1,1-dimethylethoxy. The alkoxy radicals mentioned may optionally have one or more, for example 1, 2, 3 or 4, substituents other than alkyl which may be selected from halogen, e.g. fluorine, chlorine, bromine or iodine, $C_1$-$C_{10}$-alkoxy as in $C_1$-$C_{10}$-alkoxy-$C_1$-$C_{10}$-alkoxy, e.g. 2-methoxyethoxy, or $C_3$-$C_{10}$-cycloalkyl as in $C_3$-$C_{10}$-cycloalkyl-$C_1$-$C_{10}$-alkoxy, e.g. cyclohexylmethoxy.

Here and hereinbelow, cycloalkyl is a cycloaliphatic radical generally having from 3 to 10, in particular from 3 to 6 and especially from 3 to 4, carbon atoms, for example cyclopropyl, cyclobutyl, cyclopentyl, cyclohexyl, cycloheptyl, cyclooctyl, cyclononyl or cyclodecyl. The cycloalkyl radicals mentioned may optionally have one or more, for example 1, 2, 3 or 4, substituents other than alkyl which may be selected from halogen, e.g. fluorine, chlorine, bromine or iodine, or $C_1$-$C_{10}$-alkoxy, e.g. $C_1$-$C_6$-alkoxy or $C_1$-$C_4$-alkoxy. Examples of substituted cycloalkyl are in particular 4-methylcyclohexyl, 3,3,5,5-tetramethylcyclohexyl and the like.

Here and hereinbelow, $C_1$-$C_{10}$-acylamino is an alkanoyl radical which is bonded via an amino group NR''' where R''' is hydrogen or $C_1$-$C_6$-alkyl and has a linear or branched aliphatic hydrocarbon radical having generally from 1 to 10, in particular from 1 to 6 and especially from 1 to 4, carbon atoms, for example methanoylamino, ethanoylamino, n-propanoylamino, isopropanoylamino, n-butanoylamino, isobutanoylamino and tert-butanoylamino.

In a preferred embodiment, the 2-arylacetaldehydes I are 2-phenylacetaldehydes whose phenyl group optionally has one or more, for example 1, 2, 3, 4 or 5, substituents each independently selected from R' as defined above.

Such compounds can be described by the following formula Ia

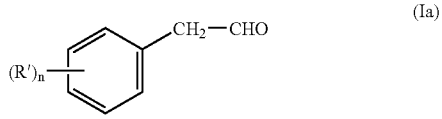

where R', when n>1, may be the same or different and be as defined above; n is 0, 1, 2, 3, 4 or 5, in particular 0, 1 or 2, and especially 1. R' is in particular selected from halogen.

In a particularly preferred embodiment, R' in the above formula Ia is halogen and n is 1. R' is then in particular arranged in the 4-position.

In a further particularly preferred embodiment, the 2-arylacetaldehyde I used is a phenylacetaldehyde. The phenylacetaldehyde used optionally has one or more substituents selected from fluorine, chlorine, bromine and iodine on the phenyl ring. Very particular preference is given to using 4-fluorophenylacetaldehyde.

The nonenolizable aldehyde compounds II used in accordance with the invention have the feature that the carbon atom in the α-position to the aldehyde group bears no hydrogen atom. Especially suitable are aromatic aldehyde compounds. The aryl group of aromatic aldehyde compounds II used in accordance with the invention may have one or more, for example 1, 2, 3, 4 or 5, substituents selected independently from R'' which is as defined above for R'.

In addition, suitable nonenolizable aldehydes II are compounds whose aldehyde group is bonded to a radical selected from $C_1$-$C_{10}$-alkyl which optionally has one or more substituents other than alkyl which may be selected from fluorine, chlorine, bromine, iodine, $C_1$-$C_{10}$-alkoxy and $C_3$-$C_{10}$-cycloalkyl;

$C_3$-$C_{10}$-cycloalkyl which optionally has one or more substituents other than alkyl which may be selected from fluorine, chlorine, bromine, iodine and $C_1$-$C_{10}$-alkoxy;

nonaromatic heterocyclyl which is optionally substituted by 1, 2, 3 or 4R' radicals as defined above; and heteroaryl which is optionally substituted by 1, 2, 3 or 4R' radicals as defined above.

Here and hereinbelow, nonaromatic heterocyclyl is a nonaromatic, heterocyclic radical generally having from 3 to 10, in particular from 3 to 6 and especially from 5 to 6, ring atoms of which typically 1, 2 or 3 are heteroatoms which are selected from oxygen, sulfur and nitrogen. Examples thereof are: tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, pyrrolidin-5-yl, piperidin-1-yl, piperidin-2-yl, piperidin-3-yl, piperidin-4-yl, morpholin-2-yl, morpholin-3-yl, morpholin-4-yl, hexahydropyridazin-1-yl, hexahydropyridazin-3-yl, hexahydropyridazin-4-yl, piperazin-1-yl, piperazin-2-yl, piperazin-3-yl, hexahydroazepin-1-yl, hexahydroazepin-2-yl, hexahydroazepin-3-yl, hexahydroazepin-4-yl, hexahydro-1,4-diazepin-1-yl, hexahydro-1,4-diazepin-2-yl, dihydrofuran-2-yl, 1,2-oxazolin-3-yl, 1,2-oxazolin-5-yl, 1,3-oxazolin-2-yl.

Here and hereinbelow, aromatic heterocyclyl is a mono- or bicyclic aromatic, heterocyclic radical generally having from 5 to 10, in particular from 3 to 9 and especially from 5 to 6, ring atoms of which typically 1, 2 or 3 are heteroatoms which are selected from oxygen, sulfur and nitrogen. Examples thereof are: furyl such as 2-furyl and 3-furyl, thienyl such as 2-thienyl and 3-thienyl, pyrrolyl such as 2-pyrrolyl and 3-pyrrolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, in addition 2-pyrazinyl, 1,3,5-triazin-2-yl and 1,2,4-triazin-3-yl, in particular pyridyl, furanyl and thienyl.

The nonenolizable aldehyde compound II used is preferably a benzaldehyde compound which optionally has on the phenyl ring one or more, for example 1, 2, 3, 4 or 5, substituents selected independently from R'' which is as defined above for R'.

Such compounds can be described by the following formula IIa

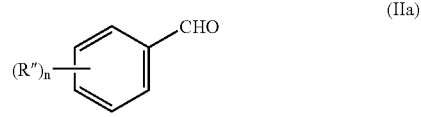

where R", when n>1, may be the same or different and is as defined above; n is 0, 1, 2, 3, 4 or 5, in particular 0, 1 or 2 and especially 1. R" is in particular selected from halogen.

In a particularly preferred embodiment, R" in the above formula IIa is halogen and n is 1. In particular, the nonenolizable aldehyde compound II used is benzaldehyde which has in the 2-position a substituent selected from fluorine, chlorine, bromine and iodine. 2-Chlorobenzaldehyde especially is used.

In a very particularly preferred embodiment, the 2-arylacetaldehyde I used is 4-fluorophenylacetaldehyde and the nonenolizable aldehyde compound II used is 2-chlorobenzaldehyde.

The reaction by the process according to the invention is advantageously effected in a mixture of at least one water-miscible organic solvent and water in which the reactants, i.e. the 2-arylacetaldehyde I and the nonenolizable aldehyde compound II, are soluble. In some cases, when the nonenolizable aldehyde compound II is only sparingly soluble, if at all, it may be sufficient that it forms a suspension or emulsion with the solvent mixture.

The solvent mixture comprises at least one water-miscible organic solvent and water in the above-specified volume ratio. The amount of the water fraction is suitably adjusted in such a way that the reaction products formed have a very low solubility in the solvent mixture (i.e. are substantially insoluble therein), while the reactants have a solubility in the solvent mixture which is sufficient to carry out the reaction. The suitable water fraction may be determined by those skilled in the art by routine experiments on the solubility.

The organic solvent and the amount of water for use in the solvent mixture according to the invention are advantageously selected in such a way that the desired cis-isomer formed as a reaction product crystallizes out of the solvent mixture as a solid under the reaction conditions.

The total amount of the solvents is generally in the range from 20 to 10 000 ml/mol, preferably in the range from 50 to 2 000 ml/mol, more preferably in the range from 100 to 1 000 ml/mol and most preferably in the range from 300 to 700 ml/mol, based in each case on the nonenolizable aldehyde compound II.

A water-miscible organic solvent refers to a solvent which forms a homogeneous mixture with water at room temperature and atmospheric pressure in the amount to be used. Preference is given to organic solvents which have unlimited miscibility with water.

The suitable water-miscible organic solvent for use in the solvent mixture according to the invention generally comprises alcohols, e.g. $C_1$-$C_4$-alkanols, diols, e.g. ethylene glycol, and polyols; ethers such as $C_1$-$C_2$-dialkyl ethers, e.g. dimethyl ether and diethyl ether; ether alcohols, e.g. ($C_1$-$C_4$-alkyl) glycols and diethylene glycol; nitriles such as $C_1$-$C_4$-alkylnitriles, e.g. methanenitrile, acetonitrile and propionitrile; and/or $C_1$-$C_2$-alkyl esters of formic acid, acetic acid or propionic acid, e.g. methyl and ethyl formate, acetate and propionate; and also dimethyl sulfoxide and/or dimethylformamide; and mixtures of the aforementioned solvents.

The organic solvent is preferably selected from $C_1$-$C_4$-alkanols such as methanol, ethanol, n-propanol, isopropanol, n-butanol, tert-butanol; and/or ($C_1$-$C_4$-alkyl) glycols, preferably mono($C_1$-$C_4$-alkyl) glycols such as methoxyethanol, ethoxyethanol, 2-methoxypropanol and 2-ethoxypropanol.

In a particularly preferred embodiment of the invention, the organic solvent is selected from methanol, ethanol, n-propanol, isopropanol, n-butanol, isobutanol, tert-butanol and/or methoxyethanol.

Bases suitable for use in the present invention include alkali metal and alkaline earth metal hydroxides such as sodium, potassium, lithium, barium and calcium hydroxides; alkali metal and alkaline earth metal alkoxides such as sodium and potassium methoxide, ethoxide, propoxide, isopropoxide, n-butoxide, isobutoxide, tert-butoxide and cyclohexoxide; alkali metal and alkaline earth metal phenoxides such as sodium and potassium phenoxide; alkali metal and alkaline earth metal carboxylates such as sodium, potassium, lithium and calcium carbonate; and also basic salts, for example of phosphoric acid or boric acid; also primary and secondary amines such as piperidine, pyrrolidine and diisopropylamine. Preference is given to using alkali metal hydroxides such as NaOH or KOH, more preferably NaOH.

The base is generally used in an amount of from 0.5 to 30 mol %, preferably from 0.5 to 20 mol %, more preferably from 1 to 15 mol % and most preferably from 2 to 12 mol %, based on the nonenolizable aldehyde compound II.

It has been found to be advantageous to carry out the reaction in the presence of an acidic cocatalyst. Particularly suitable acidic cocatalysts are NH-acidic and OH-acidic compounds having a maximum $pK_a$ in dimethyl sulfoxide of 25. The $pK_a$ is determined by methods known to those skilled in the art, as described, for example, in F. G. Bordwell, Accounts of Chem. Research 21 (1988), 456.

Especially suitable are NH-acidic compounds having a $pK_a$ in dimethyl sulfoxide in the range from 10 to 25. Examples thereof are sulfonamides such as benzenesulfonamide, methanesulfonamide or toluenesulfonamide; imides such as phthalimide and succinimide; triazoles such as 1,2,4-triazole; uracil and hydantoin. Preferred NH-acidic cocatalysts are benzenesulfonamide, methanesulfonamide and triazoles, in particular 1,2,4-triazole.

OH-acidic compounds suitable as acidic cocatalysts include inorganic acids such as phosphoric acid, their acidic salts such as dihydrogenphosphates, and boric acid; carboxylic acids, for example aliphatic $C_1$-$C_4$-carboxylic, -dicarboxylic and -hydroxycarboxylic acids such as formic acid, acetic acid, propionic acid, butyric acid, isobutyric acid, oxalic acid, malonic acid, succinic acid and lactic acid, and aromatic carboxylic and dicarboxylic acids such as benzoic acid, o-phthalic acid, m-phthalic acid and p-phthalic acid; phenols such as p-cresol and p-chlorophenol; and oximes such as ethanal oxime and propanone oxime. Preferred OH-acidic cocatalysts are benzoic acid, formic acid and boric acid.

The acidic cocatalysts used are especially benzenesulfonamide, methanesulfonamide, 1,2,4-triazole, benzoic acid, formic acid or boric acid.

The acidic cocatalyst is generally used in an amount of from 0.5 to 500 mol %, preferably from 1 to 100 mol %, more preferably from 5 to 80 mol % and most preferably from 10 to 50 mol %, based on the base.

The use of acidic cocatalysts in the process according to the invention leads to the formation of by-products such as triphenylpyran derivatives being substantially or fully prevented.

To react the 2-arylacetaldehyde I with the nonenolizable aldehyde compound II, it is advantageous to add the 2-arylacetaldehyde 1, optionally as solution or suspension, to a solution or suspension of the nonenolizable aldehyde compound II.

The solutions/suspensions of the aldehydes I and II may each contain a portion or the entire amount of organic solvent and/or each a portion or the entire amount the water used in the reaction. Typically, sufficient organic solvent or water will be used that the compounds I and II are dissolved or suspended in such a way which allows easy handling of the solutions/suspensions, in particular good meterability and good mixing. These amounts may be determined by those skilled in the art in routine experiments on the solubility. Otherwise, it is of minor importance for the implementation of the process according to the invention in which ratio the solvents and the water are divided between the solutions/suspensions of the aldehydes I and II. However, the solution/suspension of the aldehyde II preferably contains solvent and water in the above-specified ratio.

In a preferred embodiment, a portion of the nonenolizable aldehyde compound II, typically at least 50%, in particular at least 80% and more preferably the entire amount, is initially charged. Preference is given to initially charging the desired fraction of aldehyde compound II in a portion, for example at least 50% and in particular in at least 80%, or especially in the entire amount, of solvent/water mixture. This may result in a solution or suspension of the nonenolizable aldehyde compound II. It may also be advantageous to feed a portion of the organic solvent or solvent/water mixture to the reaction with the aldehyde compound I.

To prevent localized high concentrations of 2-arylacetaldehyde I, it has been found to be advantageous to undertake linear metering of the 2-arylacetaldehyde I or its solution where it is added to the solution or suspension of the nonenolizable aldehyde compound II. Linear metering refers to the continuous addition over a prolonged period of generally at least 0.5 h and in particular at least 1 h. In particular, the 2-arylacetaldehyde I or its solution is added at constant or decreasing rate over a period in the range from 0.1 h to 25 h, preferably from 0.5 h to 10 h, more preferably from 1 h to 6 h, continuously to a solution or suspension of II.

In a preferred embodiment of the invention, the addition is effected initially with constant addition rate and toward the end of the addition time, for example after from 60 to 80% by volume of I has been added, with an addition rate reduced, for example, to 0.8 times, 0.5 times or 0.1 times the original addition rate.

In a further preferred embodiment, the solution or suspension of the nonenolizable aldehyde compound II comprises the base and also optionally the acidic cocatalyst.

The reaction of the 2-arylacetaldehyde I with the nonenolizable aldehyde compound II is generally effected in the temperature range between 0 and 100° C., preferably between 5 and 50° C., more preferably between 10 and 40° C. and most preferably between 20 and 30° C.

In addition, the formation of by-products may be minimized by using nonenolizable aldehyde compound II in excess compared to the 2-arylacetaldehyde I. The molar ratio of the 2-arylacetaldehyde I to the nonenolizable aldehyde compound II is generally in the range from 1:1 to 1:10, preferably from 1:1.05 to 1:5, more preferably from 1:1.1 to 1:3 and most preferably from 1:1.12 to 1:1.30.

It is possible to isolate the desired reaction product having cis-configuration by customary processes which are known to those skilled in the art, for example precipitation, extraction or distillation.

In a preferred embodiment, the reaction product having cis-configuration is isolated by precipitation in such a way that the cis-isomer (reaction product) formed is crystallized out of the solvent mixture under the reaction conditions as a solid.

When the nonenolizable aldehyde compound II has been used in excess relative to the 2-arylacetaldehyde I, the excess nonenolizable aldehyde compound II may be fully or partly recovered from the reaction mixture. Suitable for this purpose are customary processes known to those skilled in the art, such as precipitation, extraction or distillation.

In a preferred embodiment, the nonenolizable aldehyde compound II used in excess is recovered in such a way that, after the desired reaction product has been removed, a separation of the reaction mixture into the organic and the aqueous phase is undertaken, for example by steam distillation of the reaction mixture and subsequent fractional distillation. Depending on the properties of the nonenolizable aldehyde compound II, for example dissolution and boiling behavior, it is obtained as an isolated fraction or as a mixture with the organic or the aqueous phase. When a mixture is obtained, the removal may be effected in a customary manner known to those skilled in the art, for example by precipitation, extraction or distillation.

The process according to the invention provides the 2,3-cis-substituted arylpropenals in high yields and very good purities, both based on the desired cis-configuration and with regard to the formation of undesired by-products.

EXAMPLES

Example 1

187.5 g of 2-chlorobenzaldehyde (CBA, 1.334 mol) are dissolved in a mixture of 300 g of methanol and 160 g of water. 22 ml of 16% by weight aqueous sodium hydroxide solution are added to the mixture and it is heated to 25° C. Subsequently, 148 g of 4-fluorophenylacetaldehyde (this 4-fluorophenylacetaldehyde (FPA) contains a 99.2% by weight fraction of para-fluorophenylacetaldehyde (p-FPA), which corresponds to 1.063 mol) are added dropwise with vigorous stirring in 2 h. The mixture is stirred at 20° C. for a further 1 h. The precipitated cis-2-(4-fluorophenyl)-3-(2-chlorophenyl)-propenal (DPP) is filtered off with suction at room temperature and washed with 2×100 ml of a mixture of 300 g of MeOH and 160 g of water.

After the drying, 266 g of DPP having a cis-DPP fraction of 98.9% are obtained. The content of substituted triphenylpyran (TPP) is 0.34%. The melting point of the dried product is 92.1° C.; the yield of DPP is 95.0%.

Example 2

170 g of CBA (1.209 mol) are dissolved in a mixture of 300 g of methanol and 90 g of water. To the mixture are added 28 ml of 16% by weight aqueous sodium hydroxide solution (0.13 mol) and 5 g of benzenesulfamide (0.03 mol) and it is heated to 25° C. Subsequently, 148 g of FPA (99.2% p-FPA, 1.063 mol) are added dropwise with vigorous stirring in 2 h. The mixture is stirred at 20° C. for a further 1 h and a pH of 8-10 is subsequently set using approx. 13 ml of 31.5% HCl. The precipitated DPP is filtered off with suction at room temperature and washed with 2×100 ml of a mixture of 300 g of MeOH and 160 g of water.

After the drying, 265 g of DPP having a cis-DPP fraction of 99.3% are obtained. TPP cannot be detected. The melting point of the dried product is 92.3° C.; the yield of DPP is 94.8%.

Example 3

187.5 g of CBA (1.334 mol) are dissolved in a mixture of 300 g of methanol and 130 g of water. To the mixture are added 28 ml of 16% by weight aqueous sodium hydroxide solution (0.13 mol) and 4 g of benzenesulfamide (0.03 mol) and it is heated to 25° C. Subsequently, 148 g of FPA (99.2% p-FPA, 1.063 mol) are added dropwise with vigorous stirring in 2 h. The mixture is stirred at 20° C. for a further 1 h. The precipitated DPP is filtered off with suction at room temperature and washed with 2×100 ml of a mixture of 300 g of MeOH and 130 g of water.

After the drying, 268 g of DPP having a cis-DPP fraction of 99.4% are obtained. TPP cannot be detected. The melting point of the dried product is 92.5° C.; the yield of DPP is 95.9%.

Examples 4 to 8

The procedure is that of example 2, except that the benzenesulfamide is replaced by the following H-acidic compounds: 4=1,2,4-triazole, 5=methanesulfonamide, 6=benzoic acid, 7=HCOOH, 8=$H_3BO_3$, each 30 mmol, and 35 ml of 16% by weight NaOH solution are used. The following results were obtained:

TABLE 1

| Example | Cocatalyst | Yield/% | cis-DPP contents/ area % (HPLC) | m.p./° C. |
|---|---|---|---|---|
| 4 | methanesulfonamide | 94.8 | 98.62 | 92.6 |
| 5 | 1,2,4-triazole | 94.0 | 98.21 | 92.3 |
| 6 | benzoic acid | 95.2 | 98.89 | 92.4 |
| 7 | formic acid | 94.7 | 98.53 | 91.9 |
| 8 | boric acid | 94.6 | 98.02 | 91.5 |

In no case can substituted triphenylpyran (TPP) be detected (HPLC).

Example 9

In a 1.25 $m^3$ stirred vessel, 15 l of aqueous sodium hydroxide solution (content: 16% by weight) are added at 15° C. to a solution of 154 kg of 2-chlorobenzaldehyde in 420 l of a mixture of MeOH and water (having a water content of 23.5% by weight), followed at 20-25° C. by 136 kg of 4-fluorophenylacetaldehyde (FPA, para-fraction 99.1%, by-products fraction <0.1%) over the course of 5 h. This results in precipitation of DPP. The precipitation may be completed by a continued reaction time of 1 h at 20° C.

After the separation on a skimmer centrifuge and washing with about 400 l of a 3:1 MeOH/water mixture, 260 kg are obtained having a residual moisture content of 6.6%.

The dried product has a cis-DPP content of 98.5%. The yield of cis-DPP is 95.1% based on p-FPA. Further products present are: trans-DPP: 0.8%; TPP: 0.4%; CBA: 0.2%.

A mixture of MeOH, water and CBA is obtained from the reaction mixture by steam distillation and is subsequently separated using a column into methanol and a mixture of water and 2-chlorobenzaldehyde. Chlorobenzaldehyde separates as the lower phase and can be reused.

Examples 10-13

The procedure is that of example 1, except using 300 g of the organic solvents specified below and with the addition of the amounts of water below. The following results were obtained:

TABLE 2

| Example | Solvent | Water/g | Yield/% | cis-DPP content/ area % (HPLC) | m.p./° C. |
|---|---|---|---|---|---|
| 10 | tert-butanol | 150 | 66.2 | 99.49 | 95.4 |
| 11 | ethanol | 100 | 88.2 | 97.80 | 91.5 |
| 12 | n-propanol | 125 | 75.5 | 99.60 | 95.3 |
| 13 | methyl glycol | 100 | 81.9 | 99.73 | 93.8 |

Example 14

Comparative example (to DE 37 22 886)

4.0 g of NaOH are dissolved in 250 ml of MeOH and admixed with cooling with 155 g of CBA. Subsequently, 138 g of FPA are added at 20-30° C. within 4-5 h. The mixture is stirred at 20° C. for a further 5 h and worked up as follows:
a) Filtering off the precipitated product with suction, washing with MeOH/water (2:1) and drying.
   Total yield of DPP: 67.6%; cis-DPP content: 93.0% (GC). The melting point is 88.4° C.
b) A pH of 7 is set using 10% $H_2SO_4$, the organic products are taken up in 600 ml of methyl tert-butyl ether, washed twice with 200 ml of water and dried over $Na_2SO_4$, and then HPLC is used to determine the amount and the composition of the resulting mixture.
   Composition: DPP: 90.6%; cis-DPP: 77.4%; trans-DPP: 13.2%; by-products: 9.2%; DPP yield (calculated, not isolated): 235 g (90.1%).

We claim:

1. A process for preparing 2,3-cis-substituted 2-arylpropenals by condensing a 2-arylacetaldehyde I with a nonenolizable aldehyde compound II in the presence of a base, which comprises carrying out the reaction in a solvent mixture which includes at least one water-miscible organic solvent and water in a $V_{solvent}:V_{water}$ volume ratio of from 10:1 to 0.5:1 and wherein the 2-arylacetaldehyde I and the nonenolizable aldehyde compound II are used in a molar I:II ratio in the range from 1:1.05 to 1:5.

2. The process as claimed in claim 1, wherein the organic solvent is selected from $C_1$-$C_4$-alkanols or/and mono($C_1$-$C_4$-alkyl) glycols.

3. The process as claimed in either of the preceding claims claim 1, wherein the base used is alkali metal or/and alkaline earth metal hydroxides.

4. The process as claimed in claim 1, wherein the base is used in an amount of from 0.5 to 30 mol %, based on the nonenolizable aldehyde compound II.

5. The process as claimed in any of the preceding claims claim 1, wherein the reaction is carried out in the presence of an acidic cocatalyst.

6. The process as claimed in claim 5, wherein the cocatalyst is used in an amount from 5 to 80 mol-%, based on the base.

7. The process as claimed in claim 5, wherein the acidic cocatalyst is selected from NH-acidic compounds having a $pK_a$ value in dimethyl sulfoxide in the range from 10 to 25, boric acid, phosphoric acid, carboxylic acids, phenols and oximes.

8. The process as claimed in claim 1, wherein the 2-arylacetaldehyde I is added to a solution or suspension of the nonenolizable aldehyde compound II.

9. The process as claimed in claim 1, wherein the 2-arylacetaldehyde I and the nonenolizable aldehyde compound II are used in a molar I:II ratio in the range from 1:1.1 to 1:3 and, optionally, excess nonenolizable aldehyde compound II is fully or partly recovered.

10. The process as claimed in claim 1, wherein the 2-arylacetaldehyde I used is phenylacetaldehyde which optionally has one or more substituents selected from fluorine, chlorine, bromine and iodine on the phenyl ring.

11. The process as claimed in claim 1, wherein the nonenolizable aldehyde compound II is benzaldehyde which optionally has one or more substituents on the phenyl ring which are selected from
- $C_1$-$C_{10}$-alkyl which optionally has one or more substituents other than alkyl which may be selected from fluorine, chlorine, bromine, iodine, $C_1$-$C_{10}$-alkoxy or $C_3$-$C_{10}$-cycloalkyl;
- $C_1$-$C_{10}$-alkoxy which optionally has one or more substituents other than alkyl which may be selected from fluorine, chlorine, bromine, iodine, $C_1$-$C_{10}$-alkoxy and $C_3$-$C_{10}$-cycloalkyl;
- $C_3$-$C_{10}$-cycloalkyl which optionally has one or more substituents other than alkyl which may be selected from fluorine, chlorine, bromine, iodine and $C_1$-$C_{10}$-alkoxy;
- phenoxy which is optionally substituted by 1,2,3,4 or 5 groups selected from $C_1$-$C_4$-alkyl, $C_1$-$C_4$-alkoxy, fluorine, chlorine, bromine and iodine;
- halogen which is selected from fluorine, chlorine, bromine and iodine;
- $C_1$-$C_{10}$-acylamino; and
- a nitro group.

12. A process as claimed in claim 1, wherein the 2-arylacetaldehyde I used is 4-fluorophenylacetaldehyde and the nonenolizable aldehyde compound II used is 2-chlorobenzaldehyde.

13. The process as claimed in claim 2, wherein the base used is alkali metal or/and alkaline earth metal hydroxides.

14. The process as claimed in claim 2, wherein the base is used in an amount of from 0.5 to 30 mol %, based on the nonenolizable aldehyde compound II.

15. The process as claimed in claim 3, wherein the base is used in an amount of from 0.5 to 30 mol %, based on the nonenolizable aldehyde compound II.

16. The process as claimed in claim 2, wherein the reaction is carried out in the presence of an acidic cocatalyst.

17. The process as claimed in claim 3, wherein the reaction is carried out in the presence of an acidic cocatalyst.

18. The process as claimed in claim 4, wherein the reaction is carried out in the presence of an acidic cocatalyst.

19. The process as claimed in claim 6, wherein the acidic cocatalyst is selected from NH-acidic compounds having a $pK_a$ value in dimethyl sulfoxide in the range from 10 to 25, boric acid, phosphoric acid, carboxylic acids, phenols and oximes.

20. The process as claimed in claim 2, wherein the 2-arylacetaldehyde I is added to a solution or suspension of the nonenolizable aldehyde compound II.

* * * * *